United States Patent
Remple et al.

(10) Patent No.: US 9,470,644 B2
(45) Date of Patent: Oct. 18, 2016

(54) DEVICES AND METHODS FOR FACILITATING USB CHARGER DETECTION

(71) Applicant: QUALCOMM Incorporated, San Diego, CA (US)

(72) Inventors: Terrence Brian Remple, San Diego, CA (US); Devdutt Patnaik, San Diego, CA (US); Jay Yu Jae Choi, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 320 days.

(21) Appl. No.: 14/083,234

(22) Filed: Nov. 18, 2013

(65) Prior Publication Data
US 2015/0137791 A1    May 21, 2015

(51) Int. Cl.
| | | |
|---|---|---|
| *H02J 7/00* | (2006.01) | |
| *G01N 27/00* | (2006.01) | |
| *G06F 1/26* | (2006.01) | |
| *G01R 19/00* | (2006.01) | |

(52) U.S. Cl.
CPC ............ *G01N 27/00* (2013.01); *G01R 19/0084* (2013.01); *G06F 1/26* (2013.01); *H02J 7/0052* (2013.01); *H02J 2007/0062* (2013.01)

(58) Field of Classification Search
CPC ....... Y02E 60/12; H02J 7/0068; H02J 7/022; H02J 7/0073; H01M 10/44
USPC ......................................................... 320/137
See application file for complete search history.

(56) References Cited

U.S. PATENT DOCUMENTS

| | | | |
|---|---|---|---|
| 6,351,809 B1* | 2/2002 | St. Pierre, Jr. ...... | G06F 13/4068 710/10 |
| 8,362,741 B2 | 1/2013 | Capella | |
| 2003/0115400 A1* | 6/2003 | Hoshino ............. | G06F 13/4081 710/305 |
| 2010/0070659 A1 | 3/2010 | Ma et al. | |
| 2012/0119696 A1 | 5/2012 | Picard | |
| 2012/0210146 A1 | 8/2012 | Lai et al. | |
| 2013/0054983 A1* | 2/2013 | Zhou ...................... | G06F 1/266 713/300 |
| 2013/0082644 A1 | 4/2013 | Gagne et al. | |
| 2013/0113414 A1 | 5/2013 | Chen et al. | |

OTHER PUBLICATIONS

"Battery Charging Specification," Revision 1.2, Dec. 7, 2010, pp. 71.
International Search Report and Written Opinion—PCT/US2014/064297—ISA/EPO—Feb. 4, 2015.

* cited by examiner

Primary Examiner — Arun Williams
(74) Attorney, Agent, or Firm — Loza & Loza, LLP (57) ABSTRACT

Electronic devices are adapted to facilitate detection of a type of USB charger to which an electronic device is connected. According to one example, an electronic device can apply a current source to a data line of a USB plug coupled to a USB port. A determination can be made whether the data line has gone to a LOW state or remained at a HIGH state after a predetermined period of time. If the data line has gone to a LOW state, the USB port may be identified as a downstream port, such as a standard downstream port (SDP) or a charging downstream port (CDP). If the data line has remained at the HIGH state, the USB port may be identified as a dedicated charging port (DCP), no matter if it is compliant or non-compliant with the BC 1.2 spec. Other aspects, embodiments, and features are also included.

27 Claims, 9 Drawing Sheets

FIG. 11

DEVICES AND METHODS FOR FACILITATING USB CHARGER DETECTION

TECHNICAL FIELD

The technology discussed below relates generally to electronic devices employing batteries rechargeable via a USB connection, and more specifically to methods and devices for facilitating detection of the type of USB charger to which an electronic device is connected.

BACKGROUND

Many electronic devices employ external ports for various reasons, such as for data, charging, or both data and charging. Over time Universal Serial Bus (USB) ports have become as much a standard for connecting power to electronic devices as it has for serial data communications. Recently the power aspects of USB have been extended to cover battery charging as well as AC adapters and other power sources. A tangible benefit of this wide-spread use is the emergence of interchangeable plugs and adapters for charging and powering portable devices. This, in turn, allows charging from a far wider variety of sources than in the past when each device required a unique adapter.

Generally, there has been a trend towards the standardization of charging ports for electronic devices. The battery-charging standard, USB Battery Charging 1.2 specification (referred to herein as "BC 1.2 spec"), defines several types of charging ports, including a dedicated charging port (DCP), a charging downstream port (CDP), and a standard downstream port (SDP). Each of these different types of charging ports are defined by the BC 1.2 spec as providing different charging (and data) capabilities.

Although there has been a trend towards the standardization for USB charging ports, many different types of charging ports that do not comply with the BC 1.2 spec still exist with different power capabilities. Many of these non-compliant charging ports can be incorrectly detected by an electronic device using the charger detection algorithm defined by the BC 1.2 spec. In many examples, incorrectly identifying the type of charging port can translate to the charger being utilized at a decreased operating current, which may increase the charge time of the electronic device or even result in charging becoming defunct.

BRIEF SUMMARY OF SOME EXAMPLES

The following summarizes some aspects of the present disclosure to provide a basic understanding of the discussed technology. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in summary form as a prelude to the more detailed description that is presented later.

Various examples and implementations of the present disclosure facilitate accurate detection of the type of USB charging port connected to an electronic device. According to at least one aspect of the disclosure, electronic devices may include a charger detector adapted to apply a current source to a data line of a USB plug coupled to a USB port. The charger detector may determine whether the data line has gone to a LOW voltage state or remained at a HIGH voltage state after a predetermined period of time while any pull-down resistor on the other data line is disabled. If the data line changes to the LOW voltage state, the charger detector can identify the USB port as a downstream port. If the data line remains at the HIGH voltage state, the charger detector can identify the USB port as a dedicated charging port.

Further aspects provide methods operational on electronic devices and/or electronic devices including means to perform such methods. One or more examples of such methods may include applying a current source to a data line of a USB plug coupled to a USB port while maintaining any pull-down resistor on the other data line disabled. A determination may be made whether the data line has gone to a LOW state or remained at a HIGH state. When it is determined that the data line changes to the LOW state, the USB port may be identified as a downstream port. When it is determined that the data line remains at the HIGH state, the USB port may be identified as a dedicated charging port.

Still further aspects include processor-readable storage mediums comprising programming operational on a processing device, such as an electronic device. According to one or more examples, such programming may be adapted for causing a processing circuit to apply a current source to a data line of a USB plug coupled to a USB port. The programming may further be adapted to cause a processing circuit to determine whether the data line has gone to a LOW voltage state or remained at a HIGH voltage state after a predetermined period of time. The programming may further be adapted to cause a processing circuit to identify the USB port as a downstream port when the data line changes to the LOW voltage state, and to identify the USB port as a dedicated charging port when the data line remains at the HIGH voltage state.

Additional examples and implementations of the present disclosure facilitate efficient detection of a proprietary USB charging port connected to an electronic device. According to at least one aspect of the disclosure, electronic devices may include a charger detector adapted to apply a current source to a data plus line of a USB plug coupled to a USB port, and enable a pull-down resistor on a data minus line of the USB plug. The charger detector may further detect that the data plus line remains at a HIGH voltage for a predetermined period of time. In response to the detection that the data plus line remained at a HIGH voltage for the predetermined period of time, the USB port may be identified as a proprietary charging port.

Further aspects provide methods operational on electronic devices and/or electronic devices including means to perform such methods. One or more examples of such methods may include applying a current source to a data plus line of a USB plug coupled to a USB port, and enabling a pull-down resistor on a data minus line of the USB plug. A determination may be made that the data plus line remains at a HIGH state for a predetermined period of time. In response to the determination that the data plus line remained at a HIGH state for the predetermined period of time, the USB port may be identified as a proprietary charging port Other aspects, features, and embodiments associated with the present disclosure will become apparent to those of ordinary skill in the art upon reviewing the following description in conjunction with the accompanying figures.

DETAILED DESCRIPTION

The description set forth below in connection with the appended drawings is intended as a description of various configurations and is not intended to represent the only configurations in which the concepts and features described herein may be practiced. The following description includes specific details for the purpose of providing a thorough understanding of various concepts. However, it will be apparent to those skilled in the art that these concepts may be practiced without these specific details. In some instances, well known circuits, structures, techniques and components are shown in block diagram form to avoid obscuring the described concepts and features.

Overview

Various features and aspects of the present disclosure facilitate accurate detection of the type of USB charging port connected to an electronic device. An electronic device can determine what type of USB port it is coupled to by applying a current source to a data line, while a pull-down resistor (if any) on the other data line is disabled. The electronic device can identify the USB port as a dedicated charging port (DCP), including proprietary charging ports, when the data line to which the current source is applied stays at a HIGH state. When the data line goes to a LOW state, the electronic device can identify the USB port as one of a standard downstream port (SDP) or a charging downstream port (CDP).

One or more additional features and aspects of the present disclosure facilitate quick detection whether a USB charging port connected to an electronic device is a proprietary port. An electronic device can apply a current source to a data plus line while also enabling a pull-down resistor on a data minus line. If the data plus line remains at a HIGH state for a predetermined period of time, the electronic device can identify the USB port as a proprietary charging port.

Exemplary System Environment

Figure 1:
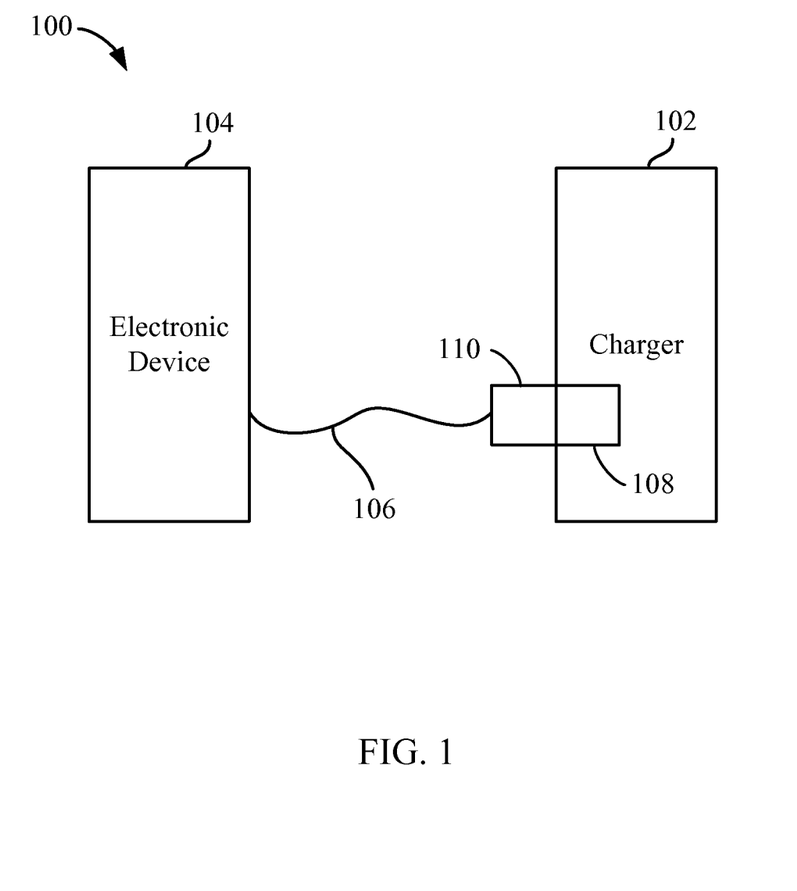
FIG. 1 is a block diagram of a system environment in which one or more aspects of the present disclosure may find application.

Referring now to FIG. 1, a block diagram of a system environment in which one or more aspects of the present disclosure may find application is illustrated. The system 100 includes a charger 102 and an electronic device 104 coupled together by a cable 106. The charger 102 includes a USB receptacle 108 configured to receive a USB plug 110 of the cable 106 to facilitate connecting the charger 102 with the electronic device 104.

The electronic device 104 may generally be a device that is adapted to recharge its battery by connecting via the cable 106 to the USB receptacle 108 of the charger 102. Example of an electronic device 104 include a mobile phone, a personal media player, a tablet computer, a smart watch, and/or other electronic device that is configured to recharge a rechargeable battery through a cable that is adapted to connect into a USB port of a charger.

Exemplary Electronic Device

Figure 2:
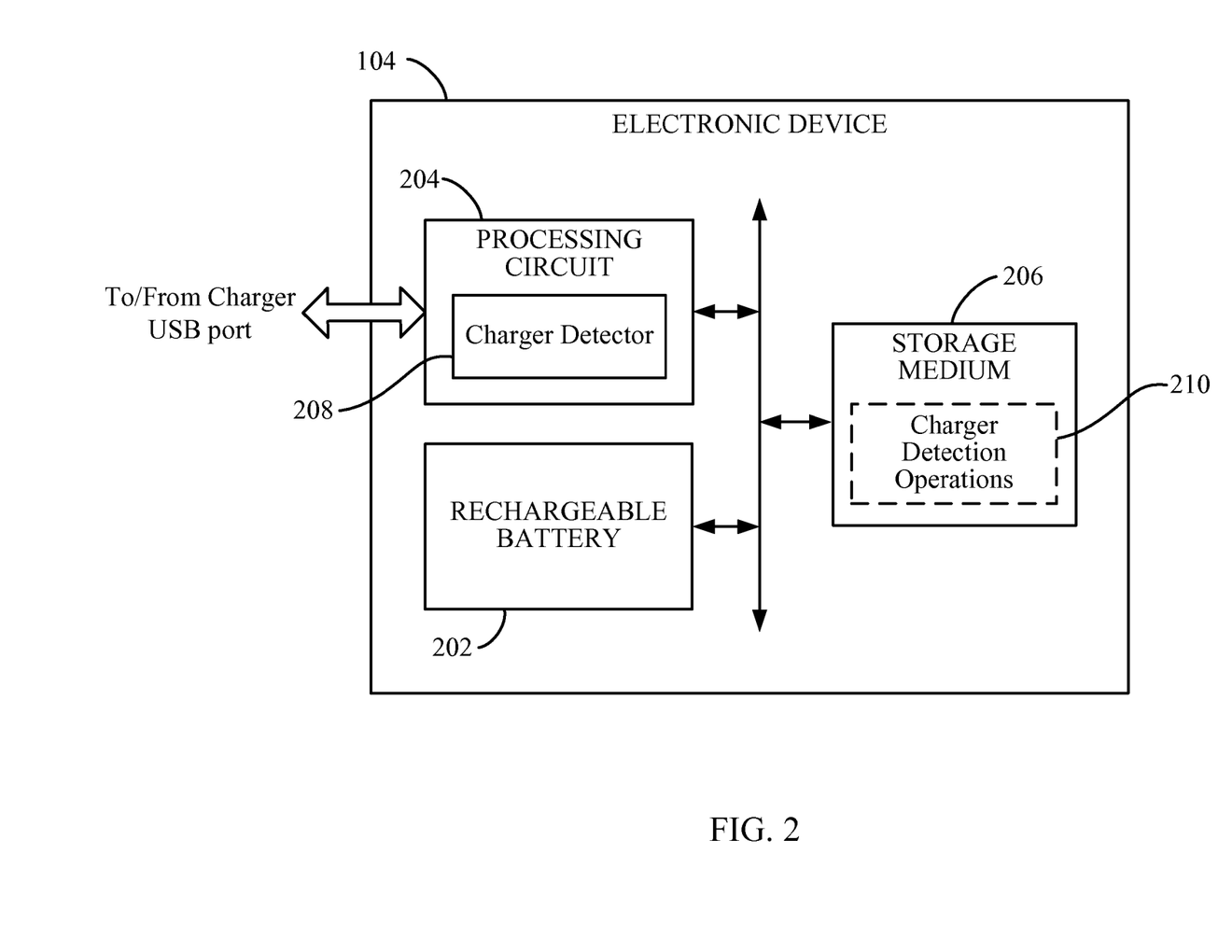
FIG. 2 is a block diagram illustrating select components of an electronic device according to at least one example.

Turning to FIG. 2, a block diagram is shown illustrating select components of an electronic device 104 according to at least one example. As shown, the electronic device 104 generally includes a rechargeable battery 202, a processing circuit 204 and a storage medium 206. The rechargeable battery 202 may be any suitable battery or plurality of batteries capable of being recharged by a USB connection to a charging device.

The processing circuit 204 is arranged to obtain, process and/or send data, control data access and storage, issue commands, and control other desired operations. The processing circuit 204 may include circuitry adapted to implement desired programming provided by appropriate media in at least one example. For example, the processing circuit 204 may be implemented as one or more processors, one or more controllers, and/or other structure configured to execute executable programming. Examples of the processing circuit 204 may include a general purpose processor, a digital signal processor (DSP), an application specific integrated circuit (ASIC), a field programmable gate array (FPGA) or other programmable logic component, discrete gate or transistor logic, discrete hardware components, or any combination thereof designed to perform the functions described herein. A general purpose processor may include a microprocessor, as well as any conventional processor, controller, microcontroller, or state machine. The processing circuit 204 may also be implemented as a combination of computing components, such as a combination of a DSP and a microprocessor, a number of microprocessors, one or more microprocessors in conjunction with a DSP core, an ASIC and a microprocessor, or any other number of varying configurations. These examples of the processing circuit 402 are for illustration and other suitable configurations within the scope of the present disclosure are also contemplated.

The processing circuit 204 is adapted for processing, including the execution of programming, which may be stored on the storage medium 206. As used herein, the term "programming" shall be construed broadly to include without limitation instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

In some instances, the processing circuit 402 may include a charger detector 208. The charger detector 208 may include circuitry and/or programming (e.g., programming stored on the storage medium 206) adapted to detect the type of USB port of a charger that the electronic device 104 is coupled to through a cable.

Figure 3:
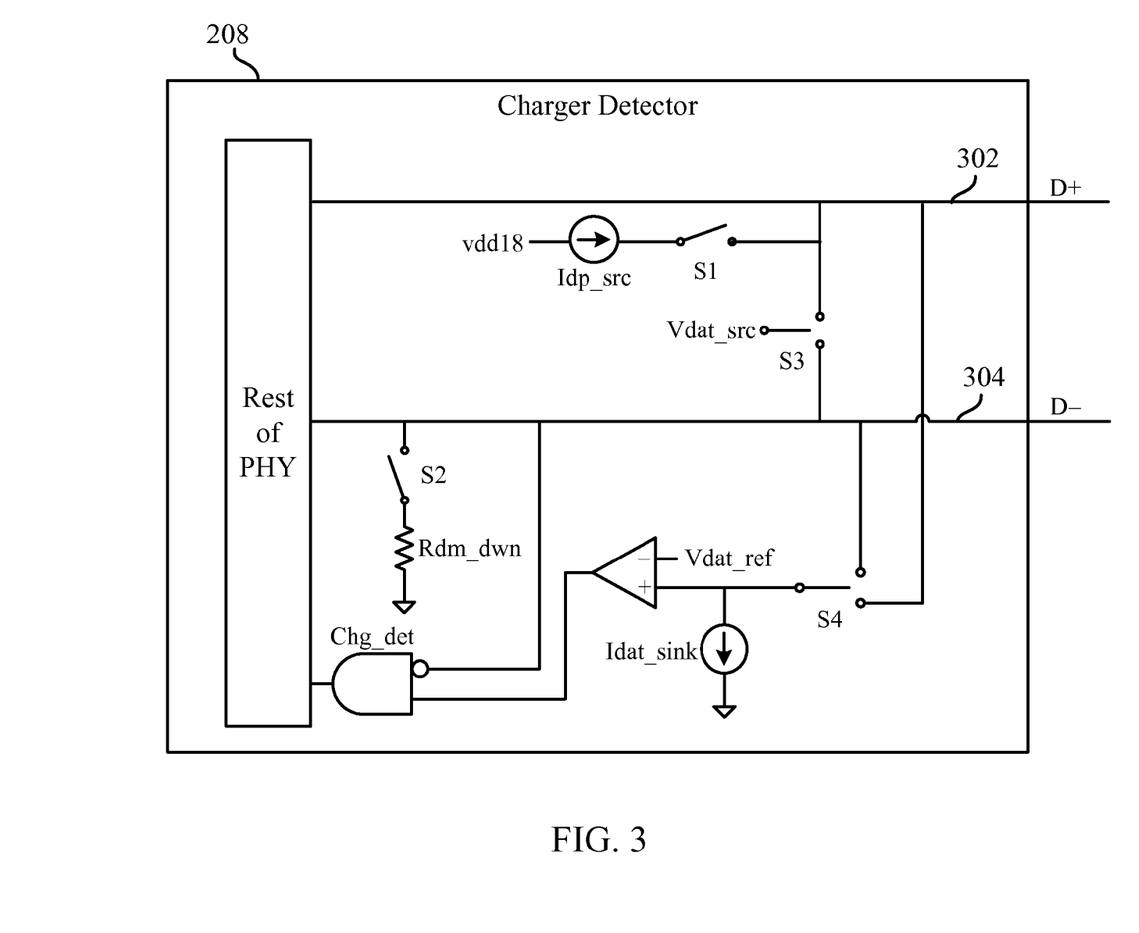
FIG. 3 is a block diagram illustrating select components of a charger detector according to at least one example.

Referring to FIG. 3, a block diagram is shown illustrating select components of a charger detector 208 according to at least one example. The example in FIG. 3 corresponds to conventional charger detection circuitry as set forth by the BC 1.2 spec. As shown, the charger detector 208 includes two data communication lines, a data plus line 302 and a data minus line 304. The data plus line 302 and the data minus line 304 correspond to the data plus and data minus connections on a typical USB connection. A current source Idp_src is coupled to the data plus line 302 with a first switch S1 positioned to control whether the current source Idp_src is applied to the data plus line 302. A data minus pull-down resistor Rdm_dwn is coupled to the data minus line 304 with a second switch S2 positioned to control whether the pull-down resistor Rdm_dwn is applied to the data minus line 304. A voltage source Vdat_src is included. The voltage source Vdat_src is typically adapted to provide a voltage in the range of about 0.5 volts and 0.7 volts. The voltage source Vdat_src can be applied to either the data plus line 302 or the data minus line 304 by use of a third switch S3. In some examples, a pull-down resistor Rdp_dwn may also be associated with the data plus line 302, including a fifth switch S5 positioned to control whether the pull-down resistor Rdp_dwn is applied to the data plus line 302. The example in FIG. 3 is just one suitable embodiment of a charger detector 208. In other embodiments, additional components, fewer components, and/or different components may be employed.

In some examples, the charger detector 208, e.g., the data plus line 302 and the data minus line 304, can interface with a USB receptacle that is adapted to receive a USB plug of a cable (e.g., the cable 106 in FIG. 1), which cable is capable of being coupled to the USB port of the charger. In other examples, the charger detector 208 can interface with the cable by a receptacle that is different from a USB receptacle, where the different receptacle receives a plug of a cable configured to be coupled with the different receptacle, and where the cable is capable of also being coupled to the USB port of the charger. In still other examples, the cable that can be coupled to a USB port of a charger may be at least substantially affixed (e.g., hardwired) to the electronic device 104, such that at least some of the wiring in the cable is run to be fixedly coupled with the charger detector 208. That is, the cable can be affixed to the electronic device 104 without any externally visible USB receptacle and USB plug. Other possible examples can include the USB cable (e.g., the cable 106 in FIG. 1) being affixed (e.g., hardwired) to the charger without any externally visible USB receptacle 108 and USB plug 110 shown in FIG. 1.

Referring again to FIG. 2, the storage medium 206 may represent one or more processor-readable devices for storing programming, such as processor executable code or instructions (e.g., software, firmware), electronic data, databases, or other digital information. The storage medium 206 may also be used for storing data that is manipulated by the processing circuit 204 when executing programming. The storage medium 206 may be any available media that can be accessed by a general purpose or special purpose processor, including portable or fixed storage devices, optical storage devices, and various other mediums capable of storing, containing and/or carrying programming. By way of example and not limitation, the storage medium 206 may include a processor-readable storage medium such as a magnetic storage device (e.g., hard disk, floppy disk, magnetic strip), an optical storage medium (e.g., compact disk (CD), digital versatile disk (DVD)), a smart card, a flash memory device (e.g., card, stick, key drive), random access memory (RAM), read only memory (ROM), programmable ROM (PROM), erasable PROM (EPROM), electrically erasable PROM (EEPROM), a register, a removable disk, and/or other mediums for storing programming, as well as any combination thereof.

The storage medium 206 may be coupled to the processing circuit 204 such that the processing circuit 204 can read information from, and write information to, the storage medium 206. That is, the storage medium 206 can be coupled to the processing circuit 204 so that the storage medium 206 is at least accessible by the processing circuit 204, including examples where the storage medium 206 is integral to the processing circuit 204 and/or examples where the storage medium 206 is separate from the processing circuit 204 (e.g., resident in the electronic device 104, external to the electronic device 104, distributed across multiple entities).

Programming stored by the storage medium 206, when executed by the processing circuit 204, causes the processing circuit 204 to perform one or more of the various functions and/or process steps described herein. For example, the storage medium 206 may include charger detection operations 210 adapted to cause the processing circuit 204 to detect the type of USB port of a charger to which the electronic device is coupled, as described herein. Thus, according to one or more aspects of the present disclosure, the processing circuit 204 is adapted to perform (in conjunction with the storage medium 206) any or all of the processes, functions, steps and/or routines for any or all of the electronic devices described herein (e.g., electronic device 104). As used herein, the term "adapted" in relation to the processing circuit 204 may refer to the processing circuit 204 being one or more of configured, employed, implemented, and/or programmed (in conjunction with the storage medium 206) to perform a particular process, function, step and/or routine according to various features described herein.

In operation the electronic device 104 may be coupled to any of a plurality of USB ports on a charger, including a dedicated charging port (DCP), a charging downstream port (CDP), or a standard downstream port (SDP). As noted previously, a DCP, CDP, and SDP all provide different charging and data capabilities. Each type of USB port is typically configured differently, so that an electronic device can detect the type of port. For example, a dedicated charging port that complies with the BC 1.2 spec (e.g., a compliant dedicated charging port (DCP)) will have specific circuitry that can be used in charger detection at the electronic device.

According to the BC 1.2 spec, an electronic device is configured to perform various stages of the port detection algorithm. Initially, the electronic device typically employs a VBUS detect stage to check that a supply bus voltage (VBUS) is asserted at an acceptable level. After the electronic device determines that the supply bus voltage is asserted, the electronic device conventionally enters a data contact detect (or DCD) stage, where a determination is made whether the data lines (data plus line 302 and data minus line 304) have made contact with the USB port. The electronic device typically performs the data contact detect stage by closing the first switch S1 in FIG. 3 to apply the current source Idp_src to the data plus line 302 for a predefined period of time, while the second switch S2 is also closed to enable the pull-down resistor Rdm_dwn on the data minus line 304.

After the data contact detect (DCD) stage, the electronic device can electrically manipulate and monitor the data lines of the port to classify the type of charger the device is coupled to. According to the BC 1.2 spec, the electronic device follows the data contact detect stage with a primary detection stage to detect whether the port is either a standard downstream port (SDP) or one of a dedicated charging port (DCP), charging downstream port (CDP), or an ACA-Dock/ACA_A. The primary detection stage is typically performed by applying the voltage source Vdat_src in FIG. 3 to the data plus line 302 by the third switch S3, and by detecting the resulting voltage on the data minus line 304 by closing the fourth switch S4 toward the data minus line 304. The voltage on the data minus line 304 is compared to a reference voltage Vdat_ref to determine whether the source voltage Vdat_src on the date plus line 302 is being conveyed to the data minus line 304. The electronic device monitors the charger detection result (Chg_det) to determine the results of the primary detection stage.

Following the primary detection stage, when the primary stage determines the port to be one of a dedicated charging port (DCP) or a charging downstream port (CDP), the electronic device can typically perform a secondary detection stage to determine whether the port is a dedicated charging port (DCP) or a charging downstream port (CDP). According to the BC 1.2 spec, the secondary detection stage is performed by applying the voltage source Vdat_src in FIG. 3 to the data minus line 304 by the third switch S3, and by monitoring the charger detection (Chg_det) result on the data plus line 302 by the fourth switch S4 being set to the data plus line 302.

Figure 4:
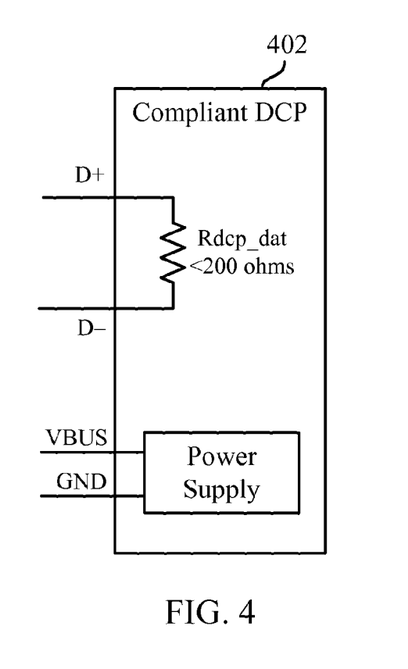
FIG. 4 is a circuit diagram illustrating select components of a compliant dedicated charging port (DCP).
Figure 5:
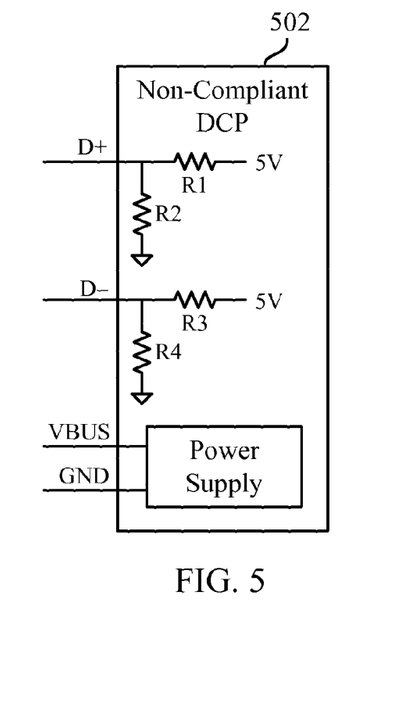
FIG. 5 is a circuit diagram illustrating select components of a first example of a non-compliant dedicated charging port (DCP).
Figure 6:
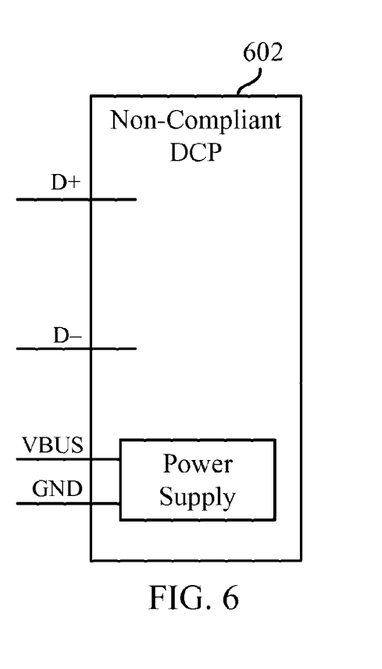
FIG. 6 is a circuit diagram illustrating select components of a second example of a non-compliant dedicated charging port (DCP).

Although a dedicated charging port that complies with the BC 1.2 spec (e.g., a compliant dedicated charging port (DCP)) will have specific circuitry that can be used in charger detection at the electronic device, other dedicated charging ports (DCPs) exist with configurations that do not comply with the BC 1.2 spec (e.g., a non-compliant dedicated charging port (DCP)). FIGS. 4 through 6 are circuit diagrams of three different examples of dedicated charging port configurations with which the electronic device 104 may be coupled.

FIG. 4 is a circuit diagram illustrating a compliant dedicated charging port 402. That is, the dedicated charging port (DCP) 402 will facilitate detection by an electronic device employing detection algorithms set forth by the BC 1.2 spec. In the BC 1.2 spec, a compliant dedicated charging port (DCP) 402 should employ a short between the data plus line (D+) and the data minus line (D–) or use a small resistance between the two, as shown in the circuit diagram of FIG. 4. During the BC 1.2 spec primary detection stage on the compliant dedicated charging port (DCP) 402, the data minus line (D–) is pulled up to about the same as the voltage source Vdat_src in FIG. 3, which is greater than Vdat_ref (typically between about 0.25 volts and 0.4 volts). This results in a high voltage at the charger detection circuit (e.g., Chg_det=1) signifying to the electronic device that it is connected to a dedicated charging port according to the BC 1.2 specification.

FIG. 5 is a circuit diagram of a first example of a non-compliant dedicated charging port (DCP) 502. In this example, an electronic device that employs detection algorithms according to the BC 1.2 spec can erroneously detect the dedicated charging port (DCP) 502 as a standard downstream port (SDP). More specifically, the data plus line (D+) and the data minus line (D–) are held at specific voltages in this example. During the primary detection stage according to the BC 1.2 spec, the dedicated charging port 502 can be erroneously detected as a standard downstream port (SDP) if the resistors used in the divider network are sufficiently high because the data minus line (D–) line can fall below the reference voltage Vdat_ref in many instances.

FIG. 6 is a circuit diagram of a second example of a non-compliant dedicated charging port (DCP) 602. In this example, an electronic device that employs detection algorithms according to the BC 1.2 spec will be erroneously detected as a standard downstream port (SDP) instead of a dedicated charging port (DCP), similar to the example in FIG. 5. More specifically, the data plus line (D+) and the data minus line (D–) are floating and have no voltage. During the primary detection stage according to the BC 1.2 spec, the dedicated charging port 602 is erroneously detected as a standard downstream port (SDP) because the data minus line (D–) will fall below the reference voltage Vdat_ref.

Typically, the misdetection as a standard downstream port (SDP) causes the electronic device to attempt to enumerate before drawing current greater than a specific level. However, since enumeration will never succeed with a dedicated charging port (DCP), the charging current remains at the low level and, as noted above, results in charging of a battery becoming defunct.

According to an aspect of the present disclosure, electronic devices are adapted to accurately detect both compliant and non-compliant dedicated charging ports (DCPs). That is, the electronic device 104 of the present disclosure may be adapted to electrically manipulate and monitor the data lines of the port in a manner to accurately detect a dedicated charging port (DCP), even when the dedicated charging port (DCP) is not compliant with the BC 1.2 spec.

Figure 7:
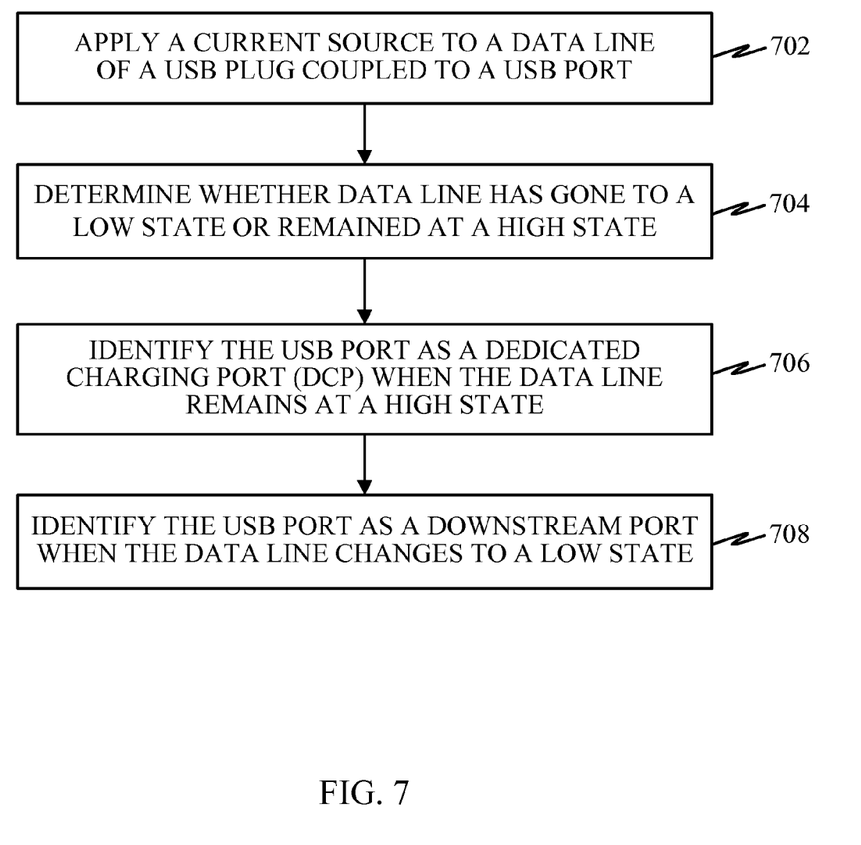
FIG. 7 is a flow diagram illustrating a method operational on an electronic device according to at least one example.

FIG. 7 is a flow diagram illustrating at least one example of a method operational on an electronic device, such as the electronic device 104. Referring to FIGS. 2, 3, and 7, an electronic device 104 can apply a current source to a data line of a USB plug coupled to a USB port at block 702. For example, the processing circuit 204 (e.g., the charger detector 208) executing the charger detection operations 210 can apply a current source to a data line of the USB plug. The current source may be a weak current source, such as about 10 micro-Amps, as defined by the BC 1.2 spec. In some implementations, the current source may be applied to the data line as part of a conventional data contact detection (DCD) stage under the BC 1.2 spec. In other implementations, the current source may be applied at any other stage of the BC 1.2 spec, or as its own stage at any placement during the BC 1.2 spec.

Figure 8:
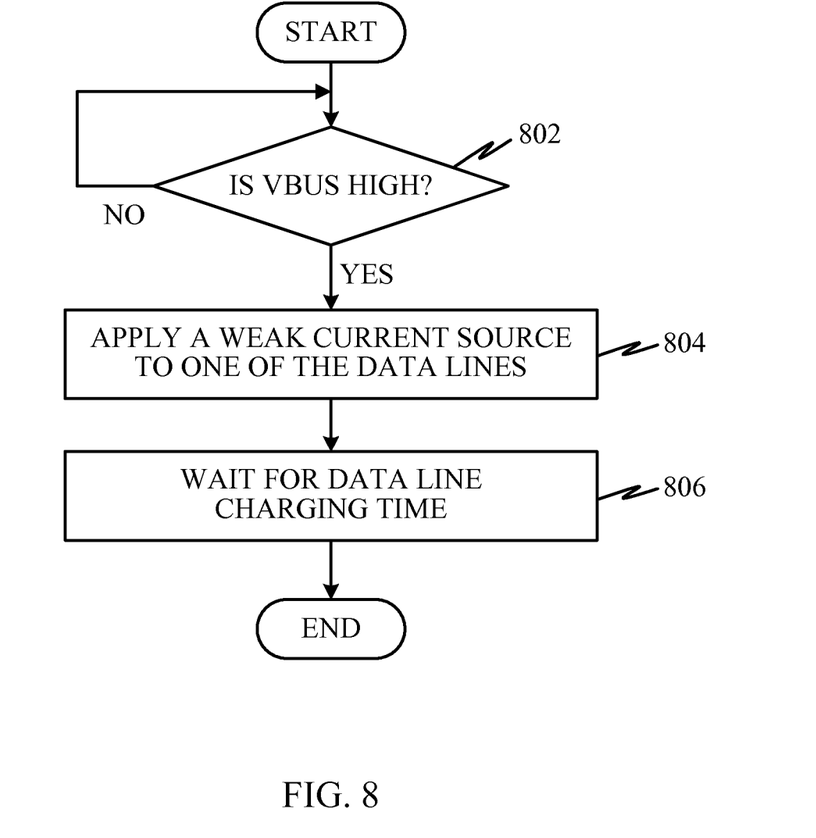
FIG. 8 is a flow diagram depicting at least one example of a process for applying the current source to the data line.

FIG. 8 is a flow diagram depicting at least one example of a process for applying the current source to the data line. This process may be implemented by the processing circuit 204 as instructed by the charger detection operations 210. Initially, a VBUS detect stage is performed, as shown by decision diamond 802. That is, the processing circuit 204 (e.g., the charger detector 208) executing the charger detection operations 210 can detect when the supply voltage (VBUS) has gone high. If the supply voltage is not asserted, the process waits until the supply voltage (VBUS) has been asserted, which indicates to the electronic device 104 that the USB plug has been connected to a port.

At operation 804, the processing circuit 204 (e.g., the charger detector 208) executing the charger detection operations 210 applies a current source to the data line. For example, the processing circuit 204 (e.g., the charger detector 208) executing the charger detection operations 210 can close the first switch S1 in FIG. 3 of the charger detector 208 to apply the current source Idp_src to the data plus line 302. According to this example, any pull-down resistor on the other data line is disabled. Thus, the processing circuit 204 (e.g., the charger detector 208) executing the charger detection operations 210 can ensure that the second switch S2 is open so that the pull-down resistor Rdm_dwn on the data minus line 304 is disabled. In another example, the processing circuit 204 (e.g., the charger detector 208) executing the charger detection operations 210 can apply the current to the data minus line 304, instead of to the data plus line 302.

At operation 806, the processing circuit 204 (e.g., the charger detector 208) executing the charger detection operations 210 waits for a data line charging time. The data line charging time is a predetermined time period that is adapted to be sufficiently long to enable the weak current source to charge capacitance on the data lines. For example, the data line charging time may be calculated from the product of the voltage and the capacitance divided by the current. Thus, when the voltage is 2 volts, the capacitance is 100 picofarads, and the current is 10 microamps, the data line charging time would be about 20 microseconds (e.g., 2 v×100 pF/10 uA=20 us).

Returning to the method depicted in the flow diagram in FIG. 7, the electronic device 104 can determine whether the data line on which the current source is applied has gone to a LOW state or remained at a HIGH state after a predetermined period of time, at 704. For example, the processing circuit 204 (e.g., the charger detector 208) executing the charger detection operations 210 can monitor the data line on which the current source is applied to determine whether the data line remains at a HIGH state or whether it goes to a LOW state. In examples where the current source is applied to the data line as part of the DCD stage, the processing circuit 204 (e.g., the charger detector 208) executing the charger detection operations 210 can wait until the timeout period has expired.

Figure 9:
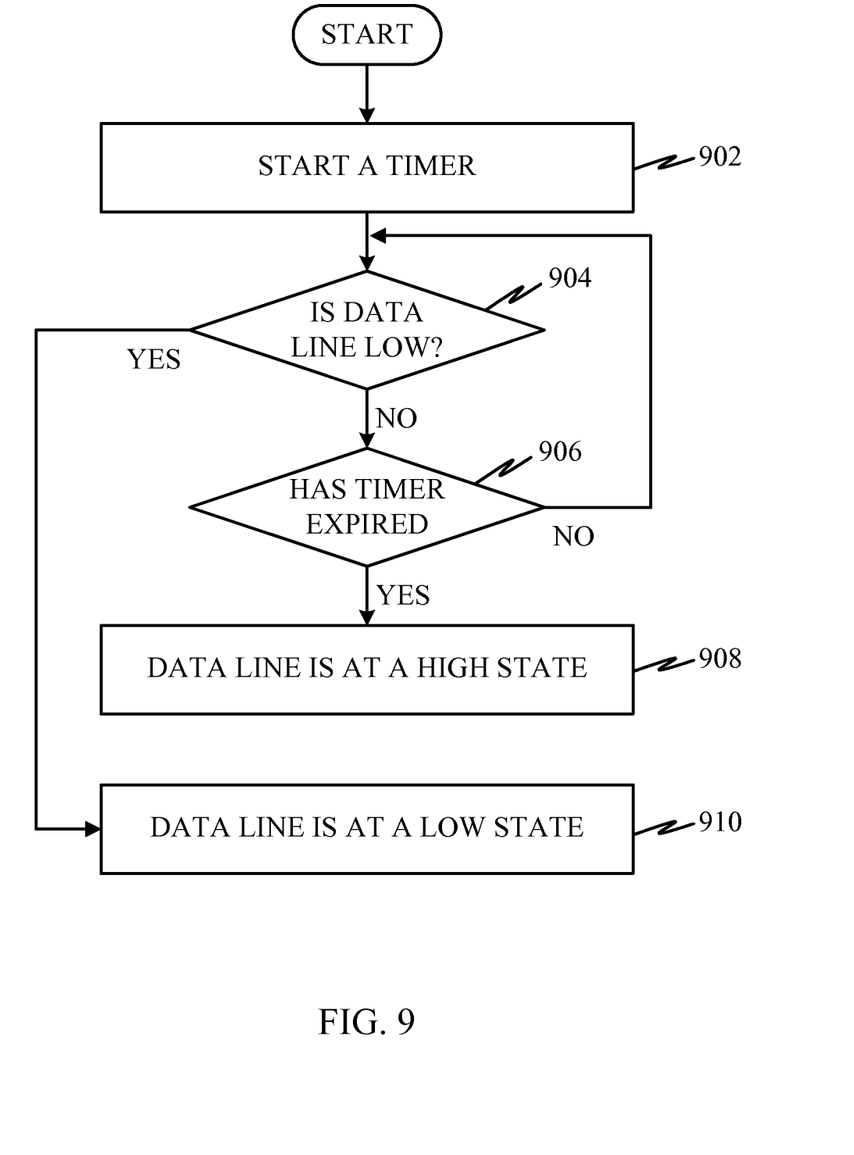
FIG. 9 is a flow diagram depicting at least one example of a process for determining whether the data line has gone to a LOW state or remained at a HIGH state.

FIG. 9 is a flow diagram depicting at least one example of a process for determining whether the data line has gone to a LOW state or remained at a HIGH state. This process may be implemented by the processing circuit 204 as instructed by the charger detection operations 210. At operation 902, the processing circuit 204 (e.g., the charger detector 208) executing the charger detection operations 210 starts a timer. In examples where the current source is applied to the data line as part of the DCD stage, the timer can represent the timeout threshold timer (Tdcd_timeout). The timer at operation 808, however, may have a duration that extends beyond the 900 millisecond maximum defined by the BC 1.2 spec for the timeout threshold timer (Tdcd_timeout). For example, the timer started at operation 808 may be set with a duration greater than 900 milliseconds. In at least one example, the timer may be set to a time duration selected from within a range of times between 901 milliseconds and 2 seconds.

At decision diamond 904, the processing circuit 204 (e.g., the charger detector 208) executing the charger detection operations 210 determines whether the data line to which the current source is applied has gone to a LOW state. If the data line has not gone to a LOW state, the processing circuit 204 (e.g., the charger detector 208) executing the charger detection operations 210 can determine whether the timer has expired at decision diamond 906. If the timer has not expired, the processing circuit 204 (e.g., the charger detector 208) executing the charger detection operations 210 returns to decision diamond 904. On the other hand, if the timer has expired at decision diamond 906 and the data line has not gone to the LOW state, then the processing circuit 204 (e.g., the charger detector 208) executing the charger detection operations 210 can determine that the data line is at a HIGH state at operation 908.

Referring back to FIG. 7, when the data line remains at a HIGH state, the electronic device 104 can identify the port as a dedicated charging port (DCP), at 706. For example, the processing circuit 204 (e.g., the charger detector 208) executing the charger detection operations 210 can identify the USB port to which the USB plug is coupled to be a dedicated charging port when the data line remains at a HIGH state for the predetermined amount of time while the current source is applied. This identification will apply to both compliant and non-compliant dedicated charging ports. For example, when the electronic device 104 is coupled to the compliant dedicated charging port (DCP) 402 depicted in FIG. 4, the data plus line 302 and the data minus line 304 in FIG. 3 will remain HIGH due to the pull-down resistor Rdm_dwn being disabled. When the electronic device 104 is coupled to the first example of a non-compliant dedicated charging port (DCP) 502 in FIG. 5, the data line (either the data plus line 302 or the data minus line 304 in FIG. 3, whichever has the current source applied thereto) will remain HIGH. Similarly, the data line on which the current source is applied will remain HIGH when the electronic device 104 is coupled to the second example of a non-compliant dedicated charging port (DCP) 602 in FIG. 6, as a result of the data lines floating in the non-compliant dedicated charging port (DCP).

Turning again to FIG. 9, the data line has gone LOW at decision diamond 904, then the processing circuit 204 (e.g., the charger detector 208) executing the charger detection operations 210 determine that the data line is at a LOW state. Turning back to FIG. 7, when the data line changes to a LOW state, the electronic device 104 can identify the port as a downstream port at block 708. For example, the processing circuit 204 (e.g., the charger detector 208) executing the charger detection operations 210 can identify the USB port to which the USB plug is coupled to be a downstream port (e.g., a standard downstream port (SDP) or a charging downstream port (CDP)) if the data line changes to a LOW state. In the example where the electronic device 104 is coupled to a downstream port (e.g., a standard downstream port (SDP) or a charging downstream port (CDP)), a pull-down resistor on the data plus line or a pull-down resistor on the data minus line inside the downstream port will cause the data line on which the current source is applied to go to a LOW state.

In various implementations, the steps of 702 through 708 can be performed as a data contact detect stage. That is, instead of the electronic device 104 performing a data contact detect stage, the steps associated with 702 through 708 may be performed. In other implementations, a conventional data contact detect stage may be performed prior to steps 702 through 708.

Figure 10:
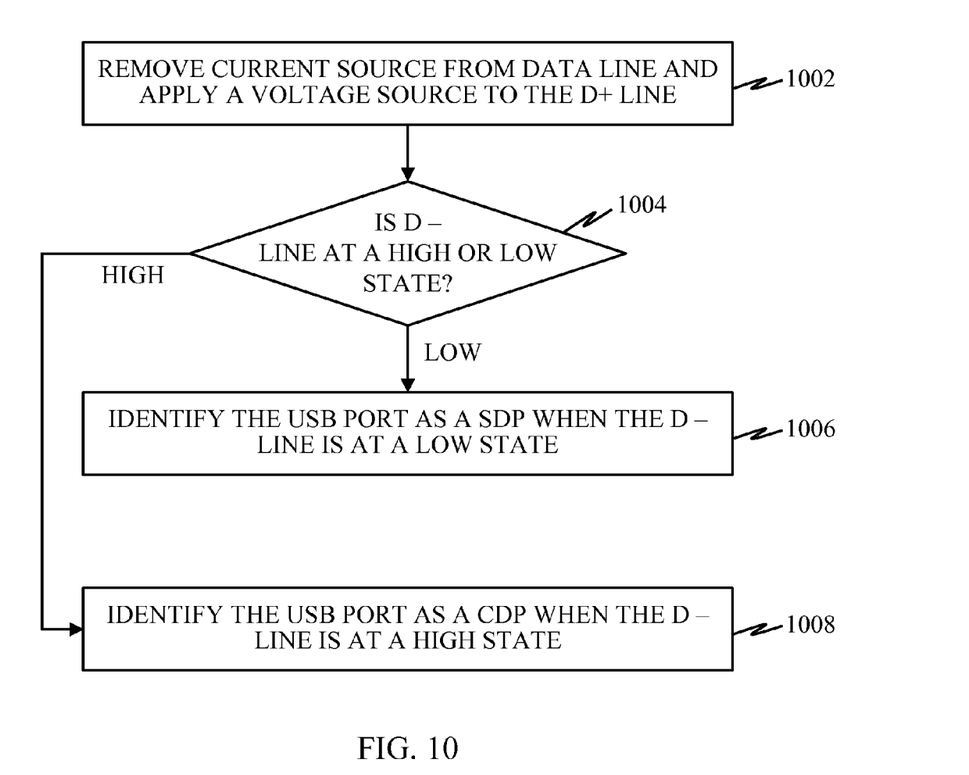
FIG. 10 is a flow diagram of a method operational on an electronic device for determining whether the downstream port is a standard downstream port (SDP) or a charging downstream port (CDP).

When the port is identified as a downstream port, the electronic device 104 can further determine whether the downstream port is a standard downstream port (SDP) or a charging downstream port (CDP). FIG. 10 is a flow diagram of a method operational on an electronic device for determining whether the downstream port is a standard downstream port (SDP) or a charging downstream port (CDP). After the electronic device has identified the USB port as a downstream port at 708 in FIG. 7, the electronic device 104 can remove the current source from the data line and can then apply a voltage source to the data plus line 302, at 1002. For example, the processing circuit 204 (e.g., the charger detector 208) executing the charger detection operations 210 can close the third switch S3 so that the voltage source Vdat_src is applied to the data plus line 302.

At 1004, the electronic device 104 can determine whether the data minus line 304 is LOW or HIGH in response to the voltage source applied to the data plus line 302. For example, the processing circuit 204 (e.g., the charger detector 208) executing the charger detection operations 210 can set the fourth switch S4 to the data minus line 304 to compare the voltage on the data minus line 304 to a reference voltage Vdat_ref in FIG. 3. If the data minus line 304 is determined to be LOW (e.g., less than the reference voltage Vdat_ref), then the processing circuit 204 (e.g., the charger detector 208) executing the charger detection operations 210 can identify the USB port as a standard downstream port (SDP) at 1006. If the data minus line 304 is determined to be HIGH (e.g., greater than or equal to the reference voltage Vdat_ref), then the processing circuit 204 (e.g., the charger detector 208) executing the charger detection operations 210 can identify the USB port as a charging downstream port (CDP) at 1008.

According to another aspect of the disclosure, electronic devices can be adapted to quickly detect whether a charging port is a compliant or non-compliant (e.g., proprietary) charging port. As noted above, a data contact detection (DCD) stage is typically employed under the BC 1.2 spec by closing the second switch S2 in FIG. 3 to enable the pull-down resistor Rdm_dwn on the data minus line 304, and the third switch S3 is closed to apply the current source Idp_src to the data plus line 302 for a predetermined period of time. Typically, the BC 1.2 spec defines the predetermined period as a Tdcd_timeout timer that is set with a duration between 300 milliseconds and 900 milliseconds.

If the timeout occurs (e.g., the time period expires without the data plus line 302 being pulled down by the pull-down resistor Rdm_dwn on the data minus line 304), the data contact detect stage is typically considered to have failed. It has been observed that the non-compliant (e.g., proprietary) dedicated charging ports, such as those depicted in FIGS. 5 and 6, result in a timeout of the data contact detection stage. Therefore, the electronic device 104 can be adapted to identify the USB port to which it is coupled as a non-compliant (or proprietary) dedicated charging port (DCP) in response to timeout at the data contact detect stage. In some examples, to ensure that there has been sufficient time for the data lines to be put into contact with the USB port, the predetermined period (e.g., the Tdcd_timeout timer) can be set to a time greater than 900 milliseconds. In at least one example, the predetermined period can be set to a value between 901 milliseconds and 2 seconds.

Figure 11:
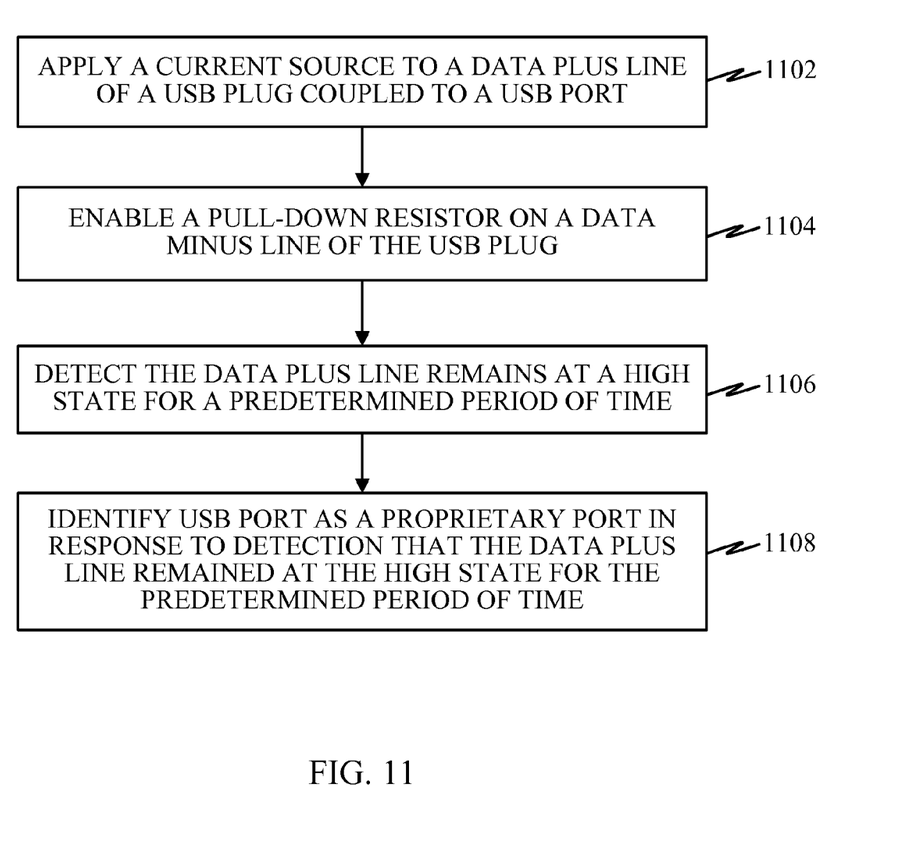
FIG. 11 is a flow diagram illustrating another method operational on an electronic device according to at least one example.

FIG. 11 is a flow diagram illustrating at least one example of another method operational on an electronic device, such as the electronic device 104. Referring to FIGS. 2, 3, and 11, an electronic device 104 can apply a current source to a data plus line of a USB plug coupled to a USB port at 1102. For example, the processing circuit 204 (e.g., the charger detector 208) executing the charger detection operations 210 can close the first switch S1 to apply a current source Idp_src to the data plus line 302.

At 1104, the electronic device 104 can enable a pull-down resistor on the data minus line of the USB plug. For example, the processing circuit 204 (e.g., the charger detector 208) executing the charger detection operations 210 can close the second switch S2 to enable the pull-down resistor Rdm_dwn on the data minus line 304.

At 1106, the electronic device 104 can detect that the data plus line remains at a HIGH state for a predetermined period of time. For example, the processing circuit 204 (e.g., the charger detector 208) executing the charger detection operations 210 can detect that the data plus line 302 remains at the high state for the duration of the Tdcd_timeout timer. As noted above, the Tdcd_timeout timer may be modified from the BC 1.2 spec to be greater than 900 milliseconds.

At 1108, the electronic device 104 can identify the USB port to which the USB plug is coupled as a proprietary or non-compliant dedicated charging port (DCP) in response to the determination that the data plus line remained at the HIGH state for the duration of the predetermined period of time. For example, the processing circuit 204 (e.g., the charger detector 208) executing the charger detection operations 210 can indicate the USB port to be a proprietary DCP in response to timeout occurring.

The features described herein and associated with FIG. 11 can be employed independently from the features described above with reference to FIG. 7. For example, the non-compliant charger detection features described herein (e.g., with reference to FIG. 11) can be employed with the conventional detection process defined by the BC 1.2 spec, where failure of the DCD stage can indicate that the port is a non-compliant dedicated charging port (DCP). In other examples, the non-compliant charger detection features described herein (e.g., with reference to FIG. 11) can be employed in combination with the dedicated charging port (DCP) detection features described herein (e.g., with reference to FIG. 7).

While the above discussed aspects, arrangements, and embodiments are discussed with specific details and particularity, one or more of the components, steps, features and/or functions illustrated in FIGS. 1, 2, 3, 4, 5, 6, 7, 8, 9, 10, and/or 11 may be rearranged and/or combined into a single component, step, feature or function or embodied in several components, steps, or functions. Additional elements, components, steps, and/or functions may also be added or not utilized without departing from the present disclosure. The apparatus, devices and/or components illustrated in FIGS. 1, 2, 3, 4, 5, and/or 6 may be configured to perform or employ one or more of the methods, features, parameters, and/or steps described in FIGS. 7, 8, 9, 10, and/or 11. The novel algorithms described herein may also be efficiently implemented in software and/or embedded in hardware.

While features of the present disclosure may have been discussed relative to certain embodiments and figures, all embodiments of the present disclosure can include one or more of the advantageous features discussed herein. In other words, while one or more embodiments may have been discussed as having certain advantageous features, one or more of such features may also be used in accordance with any of the various embodiments discussed herein. In similar fashion, while exemplary embodiments may have been discussed herein as device, system, or method embodiments, it should be understood that such exemplary embodiments can be implemented in various devices, systems, and methods.

Also, it is noted that at least some implementations have been described as a process that is depicted as a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function. The various methods described herein may be partially or fully implemented by programming (e.g., instructions and/or data) that may be stored in a machine-readable, computer-readable, and/or processor-readable storage medium, and executed by one or more processors, machines and/or devices.

Those of skill in the art would further appreciate that the various illustrative logical blocks, modules, circuits, and algorithm steps described in connection with the embodiments disclosed herein may be implemented as hardware, software, firmware, middleware, microcode, or any combination thereof. To clearly illustrate this interchangeability, various illustrative components, blocks, modules, circuits, and steps have been described above generally in terms of their functionality. Whether such functionality is implemented as hardware or software depends upon the particular application and design constraints imposed on the overall system.

The various features associate with the examples described herein and shown in the accompanying drawings can be implemented in different examples and implementations without departing from the scope of the present disclosure. Therefore, although certain specific constructions and arrangements have been described and shown in the accompanying drawings, such embodiments are merely illustrative and not restrictive of the scope of the disclosure, since various other additions and modifications to, and deletions from, the described embodiments will be apparent to one of ordinary skill in the art. Thus, the scope of the disclosure is only determined by the literal language, and legal equivalents, of the claims which follow.

What is claimed is:

1. An electronic device, comprising:
a charger detector adapted to:
apply a current source to a data line of a USB plug coupled to a USB port;
determine whether the data line has gone to a LOW voltage state or remained at a HIGH voltage state after a predetermined period of time;
identify the USB port as a downstream port when the data line changes to the LOW voltage state; and
identify the USB port as a dedicated charging port when the data line remains at the HIGH voltage state.

2. The electronic device of claim 1, wherein the charger detector is further adapted to:
perform a data contact detect stage prior to applying the current source to the data line.

3. The electronic device of claim 1, wherein the charger detector is adapted to apply the current source to the data line as part of a data contact detect stage.

4. The electronic device of claim 3, wherein the predetermined period of time comprises a Tdcd_timeout timer period set to a value selected from a group of values between 901 milliseconds and 2 seconds.

5. The electronic device of claim 1, wherein the charger detector adapted to apply the current source to the data line of the USB plug comprises the charger detector adapted to apply the current source to a data plus line of the USB plug while a pull-down resistor on a data minus line is disabled.

6. The electronic device of claim 1, wherein the charger detector adapted to apply the current source to the data line of the USB plug comprises the charger detector adapted to apply the current source to a data minus line of the USB plug.

7. The electronic device of claim 1, wherein, following identification of the USB port as a downstream port, the charger detector is further adapted to:
remove the current source from the data line;
apply a voltage source to a data plus line;
compare a data minus line to a reference voltage;
identify the USB port as a standard downstream port when the data minus line is less than the reference voltage; and
identify the USB port as a charging downstream port when the data minus line is at least substantially equal to the reference voltage.

8. A method operational on an electronic device, comprising:
applying a current source to a data line of a USB plug coupled to a USB port;
determining, via a processing circuit, whether the data line has gone to a LOW state or remained at a HIGH state;
identifying, via the processing circuit, the USB port as a downstream port when the data line changes to the LOW state; and
identifying, via the processing circuit, the USB port as a dedicated charging port when the data line remains at the HIGH state.

9. The method of claim 8, wherein applying the current source to the data line comprises applying the current source to the data line as part of a data contact detect stage.

10. The method of claim 9, wherein applying the current source to the data line as part of the data contact detect stage comprises applying the current source to the data line for a period of time greater than 900 milliseconds.

11. The method of claim 8, wherein applying the current source to the data line of the USB plug comprises applying the current source to a data plus line of the USB plug while a pull-down resistor on a data minus line is disabled.

12. The method of claim 8, wherein applying the current source to the data line of the USB plug comprises applying the current source to a data minus line of the USB plug.

13. The method of claim 8, further comprising:
identifying the USB port as a downstream port;
removing the current source from the data line;
applying a voltage source to a data plus line;
comparing a data minus line to a reference voltage;
identifying the USB port as a standard downstream port when the data minus line is less than the reference voltage; and
identifying the USB port as a charging downstream port when the data minus line is at least substantially equal to the reference voltage.

14. An electronic device, comprising:
means for applying a current source to a data line of a USB plug coupled to a USB port;
means for determining whether the data line has gone to a LOW state or remained at a HIGH state;
means for identifying the USB port as a downstream port when the data line changes to the LOW state; and
means for identifying the USB port as a dedicated charging port when the data line remains at the HIGH state.

15. The electronic device of claim 14, wherein the current source is applied to the data line as part of a data contact detect stage.

16. The electronic device of claim 14, wherein the current source is applied to a data plus line of the USB plug while a pull-down resistor on a data minus line is disabled.

17. The electronic device of claim 14, wherein the current source is applied to a data minus line of the USB plug.

18. The electronic device of claim 14, further comprising:
means for removing the current source from the data line after identifying the USB port as a downstream port;
means for applying a voltage source to a data plus line;
means for comparing a data minus line to a reference voltage;

means for identifying the USB port as a standard downstream port when the data minus line is less than the reference voltage; and means for identifying the USB port as a charging downstream port when the data minus line is at least substantially equal to the reference voltage.

19. A non-transitory processor-readable storage medium, comprising programming for causing a processing circuit to:
apply a current source to a data line of a USB plug coupled to a USB port;
determine whether the data line has gone to a LOW voltage state or remained at a HIGH voltage state after a predetermined period of time;
identify the USB port as a downstream port when the data line changes to the LOW voltage state; and
identify the USB port as a dedicated charging port when the data line remains at the HIGH voltage state.

20. The processor-readable storage medium of claim 19, wherein the current source is applied to the data line as part of a data contact detect stage.

21. The processor-readable storage medium of claim 19, wherein the current source is applied to a data plus line of the USB plug while a pull-down resistor on a data minus line is disabled.

22. The processor-readable storage medium of claim 19, wherein the current source is applied to a data minus line of the USB plug.

23. The processor-readable storage medium of claim 19, further comprising programming for causing a processing circuit to:
remove the current source from the data line after identifying the USB port as a downstream port;
apply a voltage source to a data plus line;
compare a data minus line to a reference voltage;
identify the USB port as a standard downstream port when the data minus line is less than the reference voltage; and
identify the USB port as a charging downstream port when the data minus line is at least substantially equal to the reference voltage.

24. An electronic device, comprising:
a charger detector adapted to:
apply a current source to a data plus line of a USB plug coupled to a USB port;
enable a pull-down resistor on a data minus line of the USB plug;
detect that the data plus line remains at a HIGH voltage for a predetermined period of time; and
identify the USB port as a proprietary port in response to the detection that the data plus line remained at a HIGH voltage for the predetermined period of time.

25. The electronic device of claim 24, wherein the predetermined period of time is greater than 900 milliseconds.

26. A method operational on an electronic device, comprising:
applying a current source to a data plus line of a USB plug coupled to a USB port;
enabling a pull-down resistor on a data minus line of the USB plug;
determining that the data plus line remains at a HIGH state for a predetermined period of time; and
identifying the USB port as a proprietary port in response to determining that the data plus line remained at the HIGH state for the predetermined period of time.

27. The method of claim 26, wherein the predetermined period of time is selected from a time within a range from 901 milliseconds to 2 seconds.

\* \* \* \* \*